US006870897B2

(12) United States Patent
Sari-Sarraf et al.

(10) Patent No.: US 6,870,897 B2
(45) Date of Patent: Mar. 22, 2005

(54) METHOD FOR IDENTIFICATION OF COTTON CONTAMINANTS WITH X-RAY MICROTOMOGRAPHIC IMAGE ANALYSIS

(75) Inventors: Hamed Sari-Sarraf, Lubbock, TX (US); Eric F. Hequet, Lubbock, TX (US); Ajay Pai, Bloomington, MN (US)

(73) Assignee: Texas Tech University System, Lubbock, TX (US)

( * ) Notice: Subject to any disclaimer, the term of this patent is extended or adjusted under 35 U.S.C. 154(b) by 72 days.

(21) Appl. No.: 10/294,034

(22) Filed: Nov. 14, 2002

(65) Prior Publication Data

US 2003/0123608 A1 Jul. 3, 2003

Related U.S. Application Data

(60) Provisional application No. 60/331,295, filed on Nov. 14, 2001.

(51) Int. Cl.[7] .................................................. G01N 23/06
(52) U.S. Cl. .............................. 378/53; 378/58; 378/22
(58) Field of Search .............................. 378/58, 22, 53, 378/83, 88, 146, 62, 54; 382/131; 356/238.1, 238.3

(56) References Cited

U.S. PATENT DOCUMENTS

| | | | |
|---|---|---|---|
| 4,839,943 A | | 6/1989 | Leifeld |
| 5,321,496 A | * | 6/1994 | Shofner et al. .......... 356/238.3 |
| 5,539,515 A | | 7/1996 | Shofner et al. |
| 5,544,090 A | | 8/1996 | Shofner |
| 5,646,405 A | * | 7/1997 | Nevel et al. .............. 250/341.6 |
| 5,901,198 A | | 5/1999 | Crawford |
| 5,907,394 A | | 5/1999 | Ghorashi et al. |
| 5,936,665 A | | 8/1999 | Vachtsevanos |
| 5,943,907 A | | 8/1999 | Ghorashi et al. |
| 6,023,497 A | | 2/2000 | Takahashi |
| 6,098,454 A | | 8/2000 | Ghorashi et al. |
| 6,112,131 A | | 8/2000 | Ghorashi et al. |
| 6,243,166 B1 | * | 6/2001 | Aemmer ..................... 356/430 |
| 6,683,455 B2 | * | 1/2004 | Ebbels et al. ............... 324/309 |

FOREIGN PATENT DOCUMENTS

EP 0285602 5/1998

OTHER PUBLICATIONS

B.D. Cullity, "Elements of X–Ray Diffraction," Dept. of Metallurgical Engineering & Material Science, 2nd ed., Addison–Wesley Publishing Company, Inc. (Reading, MA), p. 6–12, (1978).

R. A. Taylor, "Using High–Speed Image Analysis to Estimate Trash in Cotton," Journal of Engineering for Industry, p. 206–219 ( May 1985).

D. Veit, "Image Processing as a Tool to Improve Machine Performance and Process Control," International Journal of Clothing Science and Technology, vol. 8 ( No. 1/2), p. 66–72, (1996).

B. Xu, "Cotton Color Measurements by an Imaging Colorimeter," Textile Research Institute, vol. 68 ( No. 5), p. 351–358, (1998).

Bugao Xu, "Chromatic Image Analysis for Cotton Transh and Color Measurements," Textile Research Institute, vol 67 ( No. 12), p. 881–890, (Dec. 1997).

Frederick M. Shofner, "Evolution of the Microdust and Trash Monitor for Cotton Classification," Textile Research Institute, p. 150–156, (Feb. 1986).

* cited by examiner

*Primary Examiner*—Edward J. Glick
*Assistant Examiner*—Elizabeth Keaney
(74) *Attorney, Agent, or Firm*—Jones, Tuller & Cooper, P.C.

(57) ABSTRACT

A cotton sample is subjected to noninvasive x-ray microtomographic image analysis in order to recognize cotton contaminants in the cotton sample. The cotton contaminants are detected and classified using an x-ray microtomographic system. Once the cotton contaminants in the cotton sample are detected and classified, the cotton sample may be graded based on the type and amount of cotton contaminants present.

10 Claims, 19 Drawing Sheets

(a)          (b)

(c)

(a)

(b)

(c)

(d)

(a) (b)

(a)

(b)

METHOD FOR IDENTIFICATION OF COTTON CONTAMINANTS WITH X-RAY MICROTOMOGRAPHIC IMAGE ANALYSIS

CROSS-REFERENCE TO RELATED APPLICATIONS

This application claims the benefit, under 35 U.S.C. 119(e), of U.S. Provisional Application No. 60/331,295 filed Nov. 14, 2001, the contents of which are incorporated herein by reference.

BACKGROUND OF THE INVENTION

1. Field of the Invention

The present invention relates to a method for the identification of cotton contaminants with X-ray microtomographic image analysis.

2. Description of Related Art

As a natural fiber, cotton is subject to contamination from a variety of sources, including surrounding vegetation, insects, and materials involved in cotton harvesting and handling. The contaminants, including seed-coat fragments, bark, plastics and leaves, from these sources, which survive the ginning process, have a direct impact on the grade and, hence, the value of the cotton and its derivatives. It is at this stage in the manufacturing process that a precise measurement and identification of the cotton contaminants can improve the accuracy and repeatability of the grading operation. Furthermore, such measurements can provide the necessary feedback for optimizing both the production and the ginning processes—the latter is known to directly impact cotton's market value.

Because of the foregoing reasons, it is not surprising that the U.S. Department of Agriculture (USDA) has had a long-standing interest in the measurement of cotton contaminants in a cotton sample. This interest has in turn stimulated a significant amount of research in this area for more than six decades, leading to the development of a number of practical technologies. In general, such technologies can be categorized into two main groups: gravimetrics and surface scanners. Systems in the former group [e.g., the Shirley Analyzer and the Advanced Fiber Information System (AFIS)] accomplish their goal by separating and weighing or counting and sizing the contaminants. On the other hand, surface scanners [e.g., trashmeters of High-Volume Instruments (HVI)] capture an image of the sample surface and quantify its trash content by the subsequent analysis of that image. Recent research efforts for improving the sensitivity of these systems have generated only incremental improvements, including better separation machinery, use of color scanners and more sophisticated image analysis techniques, and more effective sample preparation mechanisms. However, despite these improvements, systems within both categories suffer from some fundamental limitations, some of which cannot be overcome. For example, gravimetric methods cannot distinguish between different trash particles. Surface scanners, which use visible or even near-infrared light for imaging, cannot penetrate the sample and, therefore, require sample preparation. Furthermore the results generated by these scanners will vary depending on the relative pose of the sample. Another fundamental limitation of all these systems is that of spatial resolution, which is currently in the 100's of microns.

The evolution of tomographic imaging dates back all the way to 1917, when an Austrian mathematician, Radon, showed that it was theoretically possible to reconstruct an object of arbitrary shape from its projections. It wasn't until 1972, however, that interest was generated in this field after the invention of the x-ray computed tomographic scanner by Hounsfield. He shared his discovery with Allan Cormack, who independently discovered some of the algorithms for image reconstruction. Hounsfield and Cormack showed that it is possible to compute high-quality, cross-sectional images with a high degree of accuracy from projections generated by passing x-rays through the object at different angles. Since then, an enormous amount of research has been conducted in the field of tomographic imaging. This has led to major improvements in the efficiency of the algorithms used in the reconstruction, the size of the volume that may be processed, the resolution, and more.

Fuzzy Logic was initiated in 1965 by Lotfi A. Zadeh, Professor of Systems Theory at the University of California, Berkeley. The most significant difference between fuzzy logic and conventional logic relates to the existence of fuzzy subsets. In conventional logic, the notion of a set of elements is based on the Law of the Excluded Middle, which states that an element is either a member of a set or not. This absence of a "middle ground" may be regarded as one of the flaws of conventional logic, one that is exploited by fuzzy logic. In fuzzy logic, an element may belong to any one of many subsets. The degree of belonging, however, should not be restricted to the values $\{0, 1\}$ as in the case of conventional logic; rather, it may take any number of intermediate values, as defined by a particular function. In fuzzy logic terminology, this function (characteristic to a subset) is known as the membership function of that set. The membership function is a continuous (or piecewise continuous) function in $[0, 1]$ and defines the degree to which an element belongs to a particular subset. In many everyday situations where conventional set representation fails, the concept of fuzzy membership functions may be applied to meaningfully describe abstract notions. Another important characteristic of fuzzy sets is that a member from the universe X may simultaneously be a member of several sets (indicated by the overlap of the membership functions).

BRIEF SUMMARY OF THE INVENTION

The present invention is a novel approach to the automatic recognition of cotton contaminants, also referred to herein as trash, in a cotton sample that overcomes the aforementioned shortcomings. The essence of this approach is the utilization of an x-ray microtomography system that employs computer vision algorithms to detect and to classify the cotton contaminants with high resolution. Tomographic imaging refers to the imaging of an object along cross-sectional slices from either transmission or reflection data collected by illuminating the object from many different directions. Tomographic imaging is distinctly different from most other common forms of imaging in that it provides the ability to reconstruct, with an extremely high spatial resolution, the internal features of an object, in a non-invasive fashion.

X-ray tomographic imaging essentially deals with reconstructing an object from its transmitted projections. A projection measured at a given angle is defined as the integral of the object in the direction specified by that angle. A projection can be thought of as the information derived from transmitted energies, when an object is illuminated at a particular angle by penetrating x-ray radiation. Different projections can be obtained by rotating the source around the object, or vice-versa. These projections are preferably recorded by a detector, or a bank of detectors, placed diametrically opposite to the source.

An important characteristic of tomographic imaging is the ability to view the internal features of an object without having to manipulate it. In this sense, the application of computed tomography lends itself very well to the automatic recognition of cotton contaminants, since the cotton sample requires no preparation or manual handling. Due to the availability of three-dimensional data, a view of the volume at various different angles may be obtained, as opposed to conventional surface imaging. The added spatial dimension also allows for the accurate extraction of shape and size information; this information is used for the purpose of trash classification. Apart from the shape and size information, the x-ray volume data also provides information regarding object density, a feature that is also used in the development of a classification procedure.

X-ray imaging is far superior to conventional imaging technologies in its ability to detect trash present within and on the surface of cotton. Through the use of x-ray imaging and image analysis techniques, it is possible to characterize the shape and size of trash with a high degree of accuracy. Another advantage of x-ray imaging relates to the spatial resolution, which being in the region of 40 microns for the preferred microtomography, allows for the detection of even the smallest particulate impurities. This feature enables the use of x-ray imaging in the assessment of cleaned cotton, and the detection of minute fragmented trash that survive the cleaning process. Finally, since x-ray tomographic imaging generates a three-dimensional representation of the cotton, it does not depend upon the position of the cotton or its contaminants with respect to the x-ray source. This relaxes the requirement of sample preparation and manual handling, imposed by conventional imaging technologies.

X-ray tomographic imaging is unprecedented in its ability to provide high-resolution imaging of the internal features of an object in a non-invasive fashion. A sample chosen for x-ray imaging requires no prior preparation and minimal handling. Due to its ability to produce three-dimensional representations of objects, accurate shape and size information may be extracted. X-ray images also provide density information that may be used in distinguishing objects from each other. It is these features of x-ray tomography that motivated the application of this technology to the detection and classification of contaminants in cotton.

BRIEF DESCRIPTION OF THE SEVERAL VIEWS OF THE DRAWINGS

The features and advantages of the present invention will become apparent from the following detailed description of a preferred embodiment thereof, taken in conjunction with the accompanying drawings, in which:

FIG. 16 shows a graph of input and output membership functions: a) mean value of the normalized truncated histogram; b) aspect ratio; and c) all of the four classes.

DETAILED DESCRIPTION OF THE INVENTION

Cotton contaminants, also referred to herein as trash, may be identified in a cotton sample using x-ray tomography or microtomography. Through the use of an x-ray microtomographic scanner and image processing algorithm, x-ray tomographic images provide very accurate information regarding the shape, size, and density of cotton contaminants. This information is preferably analyzed using a fuzzy-logic-based classification scheme to create a highly accurate contaminant analysis tool.

A microtomography system used is preferably a SkyScan-1074 x-ray scanner. This x-ray scanner is a compact, low-cost, portable x-ray scanner commonly used for non-destructive three-dimensional tomography. The scanner can achieve a maximum pixel resolution of 40 $\mu$m and can accommodate objects smaller than 30 mm in size. The preferred source is an air-cooled tube with voltage and current ranges of 5–40 kV and 0–1000 $\mu$A, respectively. The x-ray detector is preferably an 8-bit CCD camera with 768×576 elements and lens coupling to the scintillator. A personal computer preferably controls all aspects of the system's operation and is also used to store and to reconstruct the detector-generated data.

It should be noted that this system could be used to produce radiographic, as well as tomographic images of the objects of interest. In a tomographic mode, the reconstruction of the data is preferably accomplished using the fan-beam, filtered backprojection technique. On a preferred platform with dual Pentium-III processors, the reconstruction time is on the order of 5–10 seconds per cross section. Image artifacts due to beam hardening are minimized in software during the reconstruction procedure.

Figure 1:
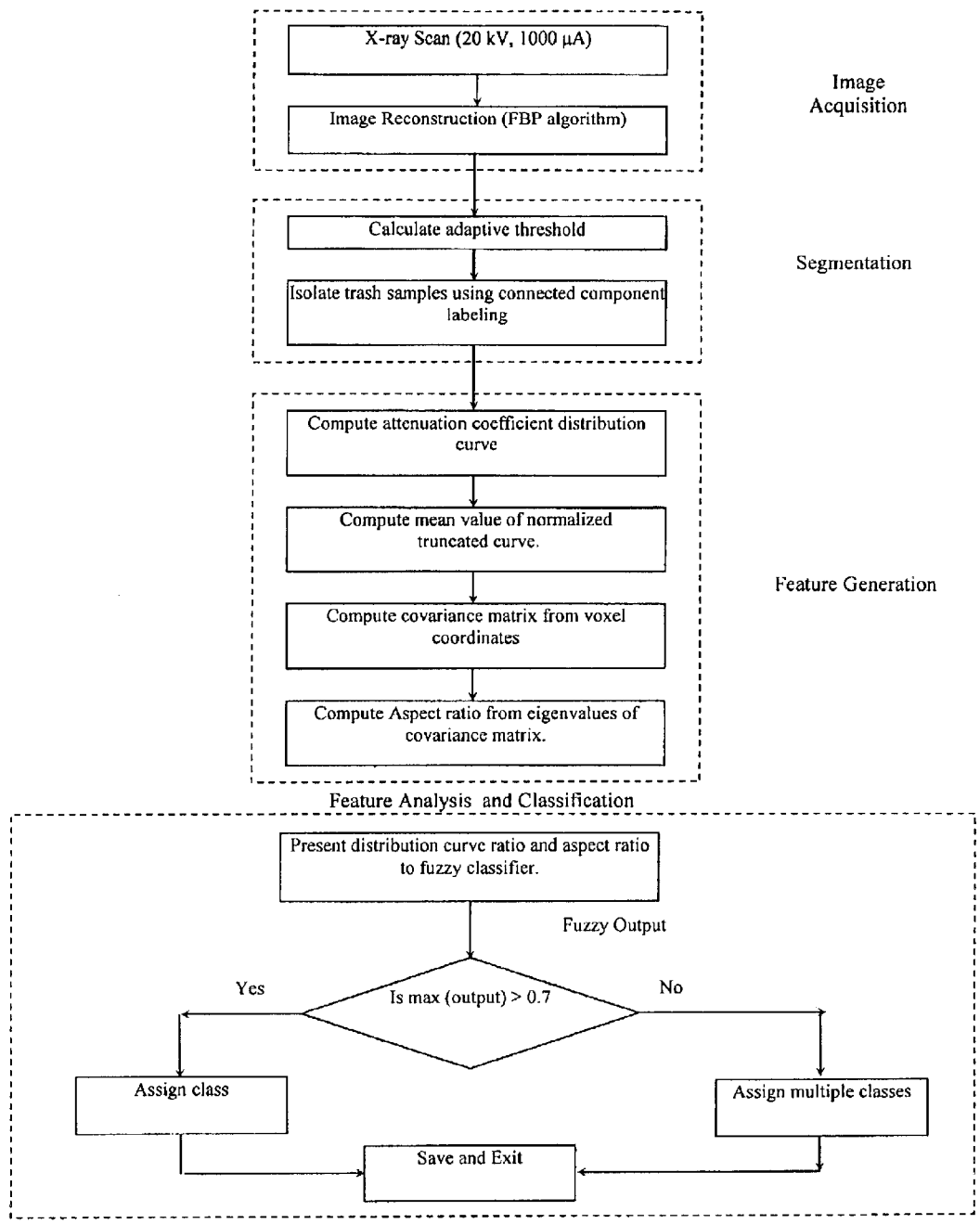
FIG. 1 is a flowchart representation of the method for identification of cotton contaminants with x-ray microtomographic image analysis.
Figure 2:
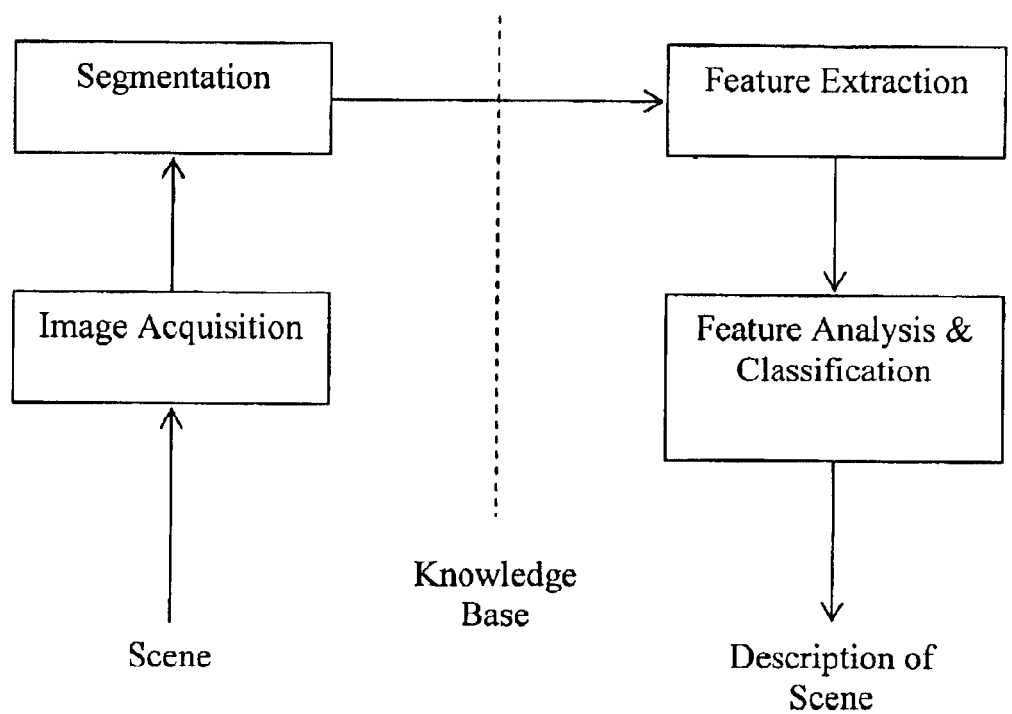
FIG. 2 is a flowchart outlining the process for designing an image classification system.

The procedure used for processing a cotton sample is outlined in the flowchart of FIG. 1. The procedure of designing almost every image classification system may roughly be divided into five stages, as depicted in FIG. 2.

The first stage consists of image acquisition. This stage may be further divided into three parts. The first part of the image acquisition involves a determination of the imaging modality to be used, and the justification of its use. The next part of the image acquisition stage involves sensor characterization, i.e., the assessment of the accuracy and the repeatability with which the chosen image acquisition system produces results. The final phase of image acquisition consists of determining the optimal settings at which the system may be operated to produce the highest quality of output.

The second stage of the image classification system design is that of image segmentation. Image segmentation can be loosely defined as the procedure by which the objects of interest in an application are isolated from the background. This is probably the most important stage of the image classification system design, and it can determine either the success or the failure of all subsequent analysis.

The output of a segmentation algorithm is usually binarized data that contains the objects of interest belonging to different classes. The next logical stage of system design would then be to determine features that effectively allow for the recognition of the individual classes. In order to accomplish this, some prior information about the classes is necessary. This a priori information about the classes is represented by the knowledge base in FIG. 2. The features measured are completely dependent on the segmented data, and hence the methods used for extracting these features are very specific to the application.

The final stage of the system design is feature analysis and classification. This stage involves the use of one of numerous available classification algorithms in order to classify the segmented objects correctly based on the features that have been extracted.

1. Image Acquisition

As mentioned above, the process of image acquisition can be divided into three distinct parts. These parts will now be further elaborated upon, with reference to the particular problem at hand.

Choice of Imaging Modality

Figure 3:
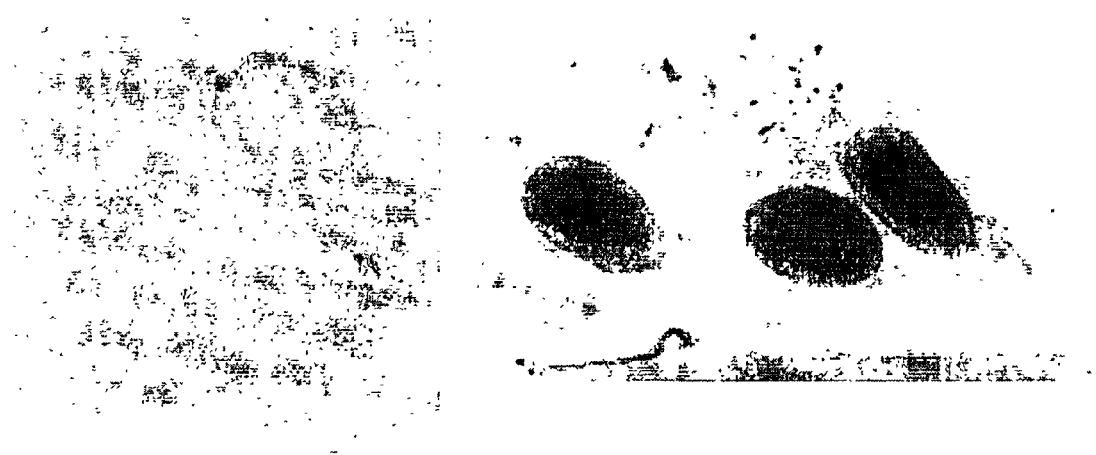
FIG. 3 shows various images of a cotton sample as follows: a) surface scan of a cotton sample; b) x-ray radiographic image of the same cotton sample; and c) x-ray tomographic representation of the same cotton.
Figure 3:

FIG. 3 shows various images of a cotton sample using different imaging techniques. FIG. 3(a) shows a simulation of the output as generated by a surface scanner. The image was generated by the high-intensity, visible-range imaging of a sample of raw seed cotton. Though seed cotton is ideally ginned prior to any form of quality assessment, the object of this experiment was simply to illustrate the inefficiency of surface imaging methods in the detection of even large trash particles, such as cotton seeds which are usually a few millimeters in diameter.

As is evident from the surface scan of a cotton sample shown in FIG. 3(a), the only trash clearly visible is particulate impurities that lie on the surface of the cotton. This inability of visible-range (or for that matter, near-infrared) imaging to detect trash content within cotton may be easily overcome by the use of high-frequency x-rays for imaging. FIG. 3(b) shows an x-ray radiographic image of the same cotton. In contrast to FIG. 3(a), the radiographic image clearly indicates the presence of trash particles, both large, and particulate, within the body of the cotton. The considerable advantage gained by using x-rays in the detection of trash is further emphasized by the region depicted in FIG. 3(b), which enables the user to detect even subtle density variations within the sample, such as the difference between mature and immature seeds.

A three-dimensional representation of the same cotton is shown in FIG. 3(c). It is obvious from FIG. 3(b) and FIG. 3(c) that x-ray imaging is far superior to conventional imaging technologies in its ability to detect trash present within and on the surface of cotton. Through the use of x-ray imaging and image analysis techniques, it is possible to characterize the shape and size of trash with a high decree of accuracy. Another advantage of x-ray imaging relates to the spatial resolution, which being in the region of 40 microns for the described microtomography system, allows for the detection of even the smallest particulate impurities. This feature enables the use of x-ray imaging in the assessment of cleaned cotton, and the detection of minute fragmented trash that survive the cleaning process. Finally, since x-ray tomographic imaging generates a three-dimensional representation of the cotton, it does not depend upon the position of the cotton or its contaminants with respect to the x-ray source. This relaxes the requirements of sample preparation and manual handling, imposed by conventional imaging technologies.

Sensor Characterization

Given the differences in density and even the chemical composition between different types of cotton contaminants, it is reasonable to hypothesize that the generated x-ray attenuation coefficients may be used as an effective, albeit not the sole, discriminatory feature between these contaminants. Prior to testing this hypothesis, however, the accuracy and the repeatability with which the described microtomography system produces attenuation coefficient numbers was assessed. To that end, the drift in the obtained attenuation coefficients of a homogeneous medium, in this case, acetone contained in a vial, was studied, both spatially and longitudinally.

Figure 4:
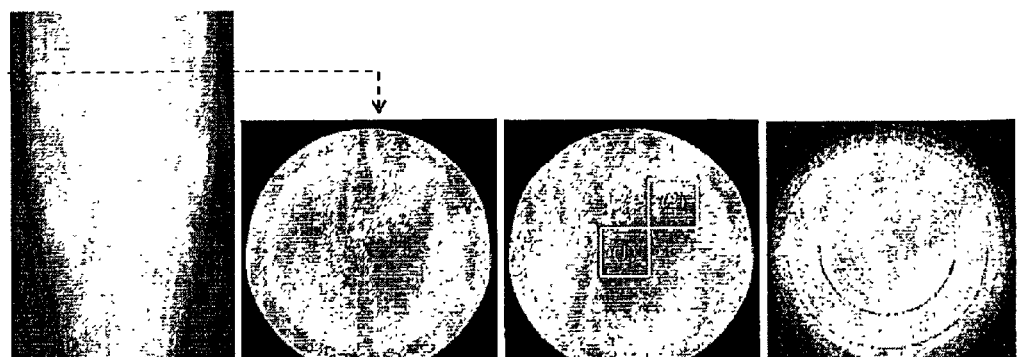
FIG. 4 are sensor characteristics obtained from a vial of acetone: a) radiographic image; b) tomographic cross section; c) image indicating two regions from which attenuation coefficient values were measured; d) ring artifacts; e) spatial variation of attenuation values and f) longitudinal variation of attenuation values.
Figure 4:
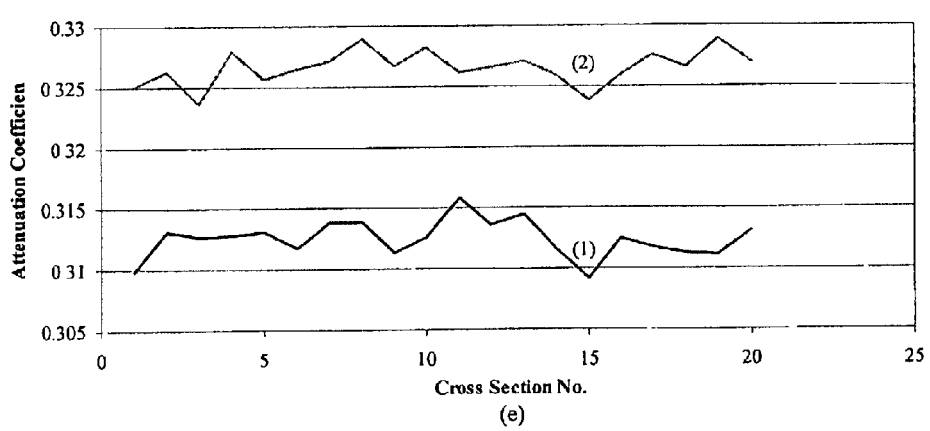
Figure 4:
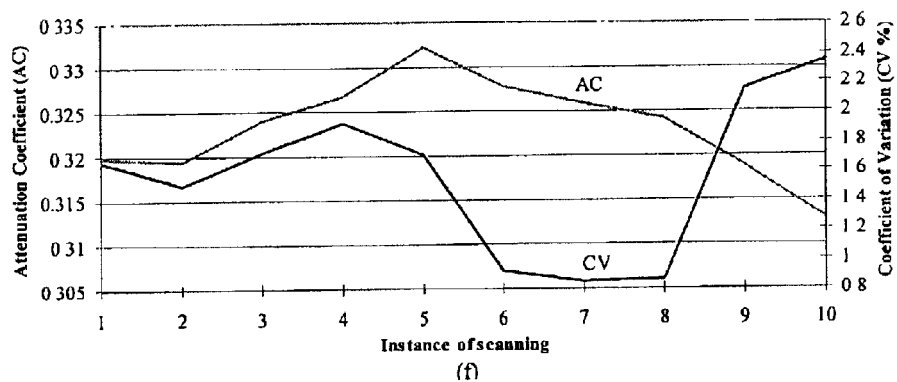

To examine the variability of the obtained values spatially, the averages of the attenuation coefficients within two regions of interest were computed over a number of slices and depicted in FIG. 4. FIG. 4(a) shows a radiographic image of the vial of acetone. FIG. 4(b) shows a tomographic cross section of the vial of acetone. FIG. 4(c) shows an image of the vial of acetone indicating two regions from which attenuation coefficient values were measured. FIG. 4(d) shows ring artifacts of the vial of acetone. FIG. 4(e) shows the spatial variation of attenuation values for the acetone, whereby each data point is the average of the values within the indicated region. FIG. 4(f) shows the longitudinal variation of attenuation values for the acetone. The offset between these two regions was produced due to the beam-hardening effect of the polychromatic x-ray beam. The statistical measure used to establish the constancy (or conversely, the variability) of the attenuation coefficients was the coefficient of variation (CV), which is defined as $$CV = \frac{\sigma}{\mu} \quad (1)$$

where $\sigma$ represents the standard deviation and $\mu$ represents the mean value of the sample data. The CV over all the cross sections is 0.5% for the lower graph and 0.4% for the upper graph.

For longitudinal analysis, the same vial of acetone was scanned over a 10-day period at irregular time intervals. Each data point on the plot of FIG. 4(f) represents an average of attenuation coefficient values over both of the indicated regions, as well as over 20 cross sections. The corresponding CV for each of the data points is also shown on the same plot. It is observed that the produced values of attenuation coefficient are quite stable within the first decimal place, both spatially and longitudinally.

Optimal Scanner Operating Point

Once the accuracy and the repeatability of the scanner output values were assessed, attention was turned toward evaluating the discriminatory power of the measured attenuation coefficients for contaminant recognition. To that end, three contaminant types were chosen: seed-coat fragments, bark, and polypropylene-based plastics. However, it should be noted that the present invention may be used to identify a wide range of cotton contaminants. The choice of these contaminants over other types is justified because they can readily survive the ginning process and show up in the yarn and the finished fabric. Samples were prepared by manually inserting multiple varieties of these trash types in pre-cleaned cotton lint. These samples were then presented to the scanner.

The measured values of the attenuation coefficient are a strong function of material density and effective atomic number, as well as the energy of the incident x-ray beam. The energy of the beam is, in turn, directly dependent on the source voltage and current. Therefore, it was necessary to establish an optimal operating point of the scanner in the presence of these samples. The optimal operating point is defined as that value of source voltage and current for which maximum contrast is achieved. Contrast is defined as the percent difference of a feature measured from the object and the background, i.e., $$\text{Contrast} = \frac{|\mu_f - \mu_b|}{\mu_b} \times 100\% \quad (2)$$

where in this case, $\mu_f$ represents the attenuation coefficient of the object measured, and $\mu_b$ represents the attenuation coefficient of the background, i.e., cotton. The expression for contrast has the disadvantage of approaching infinity for small values of $\mu_b$, as commonly observed in the case of background cotton. However, if the noise introduced by the tomographic imaging system during acquisition is assumed to be negligible (as in the case of the x-ray scanner used) the contrast measure may be replaced by the contrast difference $\Delta\mu$, which is simply given by $$\Delta\mu = |\mu_f - \mu_b| \quad (3)$$

Figure 5:
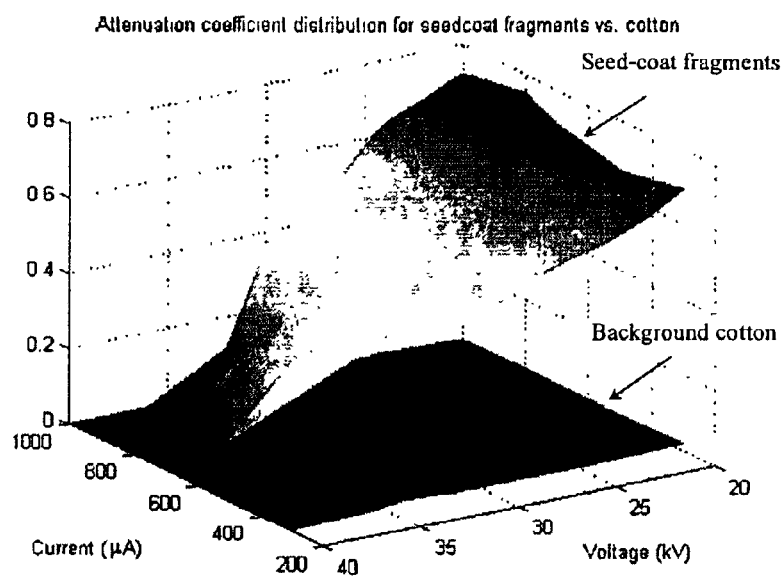
FIG. 5 shows graphs of the variation of mean attenuation values over the entire range of source voltage and current settings for a) seed-coated fragments; b) bark; c) polypropylene; and d) all classes and background cotton.
Figure 5:
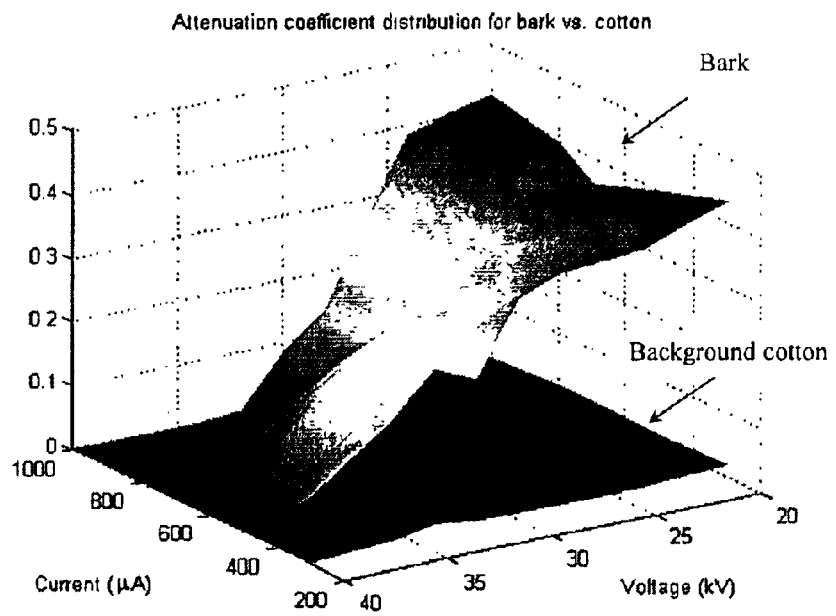
Figure 5:
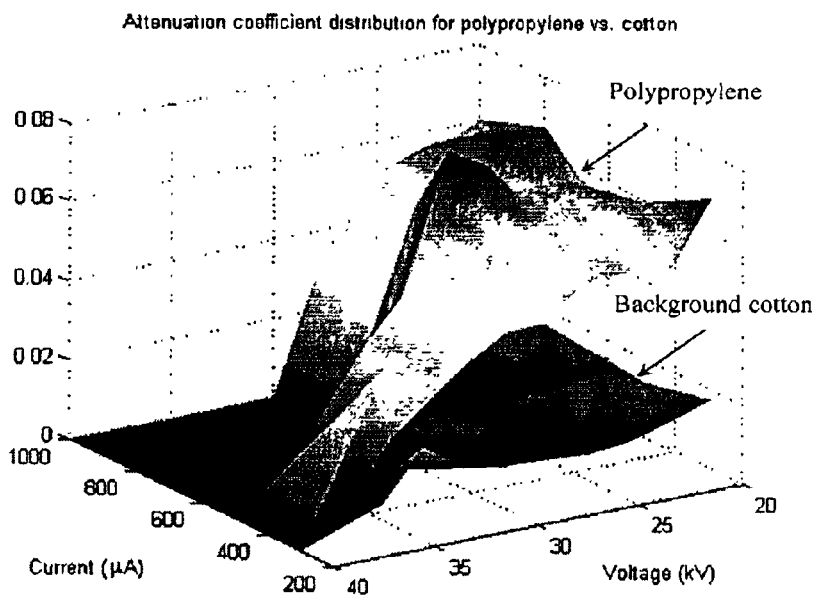
Figure 5:
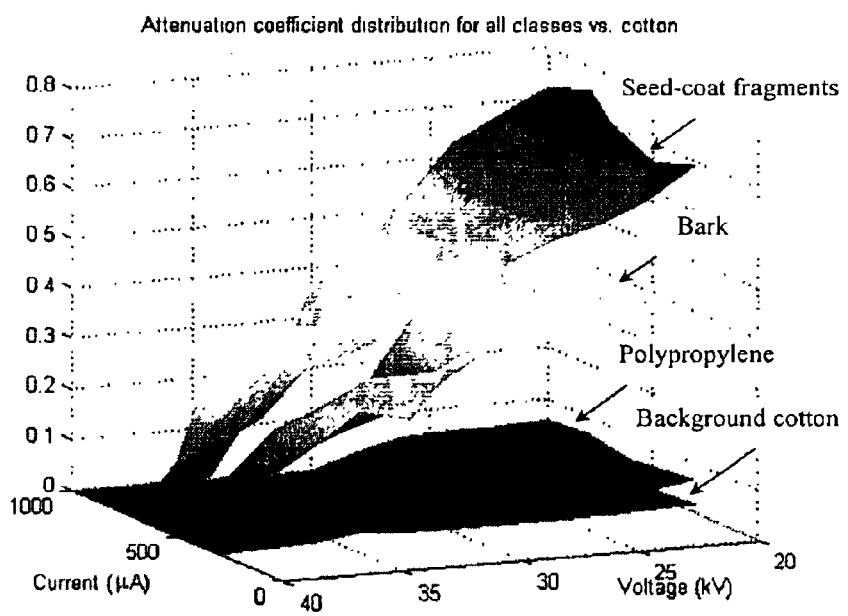

Representative samples of trash belonging to the three classes placed in pre-cleaned cotton lint were scanned at regular intervals of voltage and current across the operating range of the scanner. The choice of the particular variety of cotton used was based on its extra-long, strong and fine fibers and its minimal impurity content after processing. The results of these scans are presented in FIG. 5. FIG. 5(a) shows the results for seed-coat fragments. FIG. 5(b) shows the results for bark. FIG. 5(c) shows the results for polypropylene. FIG. 5(d) shows the results for all contaminants and background cotton.

For every volume scanned, a representative subset of the slices was chosen, roughly 6–10 slices per volume. The trash present in these cross-sectional slices was then manually segmented, and the mean attenuation coefficient value was calculated. Though this approach does not account for the attenuation coefficient variations that one might expect to see within the body of the trash, it was considered acceptable since the purpose of the scan was solely to determine the general effect that changing x-ray beam energy levels have on the measured attenuation coefficients of the trash. Since only 6–10 slices were chosen per volume, great care was taken to ensure that slice registration is maintained, so that exactly the same slices are used for segmentation in every volume. However, flat field correction (a standard procedure used to calibrate the detector sensitivity) between two different energy scans required that the sample be removed from and later re-inserted into the x-ray chamber, resulting in a slight registration error from volume to volume.

The general trend observed from the scans of FIG. 5 was that the attenuation coefficient values drop gradually with an increase in the x-ray beam energy, with a higher dependence on tube voltage. There are however, a few irregularities observed in the surfaces of FIG. 5, appearing in the form of sharp peaks. These peaks were traced back to two possible causes:

1. Due to the loss of registration from volume to volume, the slices chosen for manual segmentation may not be identical in each volume, thus creating an error in measurement.

2. Due to the random movement feature, the sample is shifted vertically in a random fashion in order to minimize the error due to defective elements in the CCD camera. In some cases, however, loss of synchronization between the sample position and the corresponding CCD elements being read causes the wrong slice to be scanned, leading to considerable error. The random movement feature was therefore turned off, alleviating this problem. Due to the inherent non-homogenous nature of the sample, there were a negligibly small amount of ring artifacts observed in the final reconstructed slices.

A study of the attenuation coefficient versus energy plots and the contrast difference measurements revealed that maximum contrast difference between the three classes and cotton is achieved at lower voltage levels. However, there were a few issues that needed to be resolved for low-energy scans. First, as the lowering of the x-ray beam energy causes an increase in the perceived attenuation coefficient values, it simultaneously causes a large number of low intensity background features to become visible. This is a serious problem, which would be expected to complicate the segmentation process. There is, however, an advantage to this phenomenon, which makes it desirable to scan cotton at really low energy levels. A low-energy scan allows for the detection of very low-density cotton neps (fiber entanglements), a major source of concern to the cotton industry. The second problem encountered in low-energy scans relates to the appearance of uniform noise throughout the slice. This noise may be attributed to the reduced number of photons emitted by the source at lower current levels, and may be mitigated to a degree by raising the tube current setting at constant tube voltage. Therefore, it was concluded that the optimal scan be performed at the lowest voltage setting, preferably 20 kV, and the highest current setting, preferably 1000 $\mu$A, so as to allow for maximum separation between the three classes of trash, while minimizing the noise.

2. Segmentation

Once the optimal operating point, preferably 20 kV, 1000 $\mu$A, was determined, the focus was shifted to the segmentation process. As in the earlier case, a number of volumes containing all three classes of trash were scanned at the chosen operating point. Each slice of the volumes was then segmented manually, and distribution curves of the attenuation coefficients for each trash class was generated. A normalized version of these curves is shown in FIG. 6.

Figure 6:
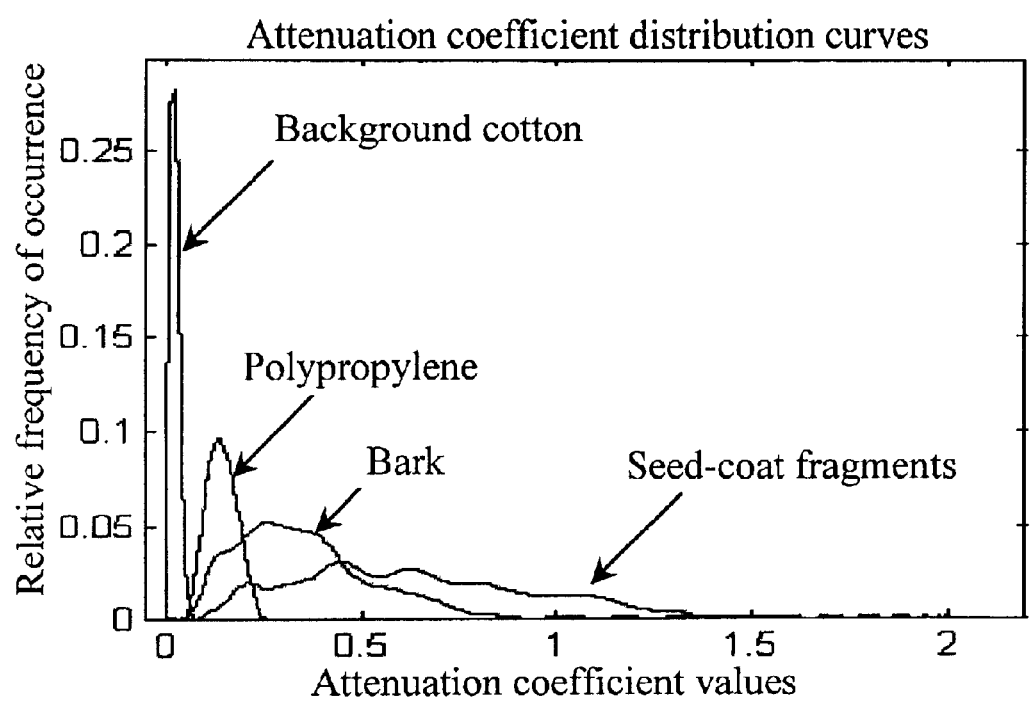
FIG. 6 is a graph of the normalized distribution curves of the attenuation coefficients for the three classes of trash.

Observations made about the distribution curves in FIG. 6 include the following. First, of the three classes, polypropylene is the only man-made contaminant. Therefore, it is expected that the polypropylene distribution shows very little variation in attenuation coefficient numbers. This is verified by FIG. 6, which indicates that of the three classes, polypropylene shows a high degree of uniformity. This attribute may be used very effectively to distinguish polypropylene from the other trash classes. Second, the seed-coat fragments show a high variance in attenuation coefficients. This may be attributed to the composition of the seed coat, which consists of a high-density shell covered on the exterior by dense, short cotton fibers that thin out as they go farther away from the seed coat. These fibers, which have a higher density than background cotton, are an integral part of the seed-coat fragment and need to be successfully segmented as part of the trash. Third, and perhaps the most interesting feature of this plot is that there appears to be a minimal overlap between the distribution of the background cotton, and the trash classes. This is extremely serendipitous, for it allows for the effective segmentation of the trash from the background by the application of a simple threshold. It was determined experimentally that the optimal value of this threshold which allows for a near complete removal of the background lies between the attenuation coefficient values of 0.07 and 0.09.

Automated Adaptive Threshold Generation

The choice of a threshold value that may be used for segmentation may be based upon two factors. The first of these is the absolute attenuation coefficient numbers as output by the x-ray scanner. The attenuation coefficient numbers are a function of the tube voltage-current response, and can therefore be expected to vary from machine to machine. Furthermore, it can also be expected that for a given machine, the attenuation coefficient numbers would experience some form of temporal output drift, leading to a change in the value of a threshold for segmentation. The second factor that influences the threshold value is the relative difference between the attenuation coefficient numbers of the background cotton and the different trash types present in the sample. This factor is in turn dependent upon many factors, principle among which are the type of cotton used (that would influence background attenuation coefficient values) for sample generation and the types of trash used in the creation of the sample (due to the considerable variation seen in the distributions of FIG. 6).

What is then required is a completely automated procedure to calculate a threshold for a given volume that is independent of the x-ray scanner used, and of any form of output drift. The procedure should also be independent of the type of background used, and of the types of trash present in the sample. In what follows, such an automated adaptive thresholding algorithm is described, along with an illustrative example.

The operation of the thresholding algorithm is based on the premise that trash content (by volume, measured in voxels) in any given sample of ginned cotton is between 5–10 percent of the entire volume. This number drops to fractional values for cleaned cotton. The algorithm centers on the isolation of the background from the trash present in the volume. It achieves this goal by using the mean value of the entire volume (trash and background cotton together) as the feature for comparison. Since the mean value of the volume varies linearly as the attenuation coefficient numbers, it is independent of the scanner specific response, and any drift in scanner output. The mean value would also vary proportionately as the density of the specific cotton type used, thus removing the dependency upon the type of background.

Now, the mean attenuation coefficient value is known to consist of contributions from two components: the trash (comprising 5–10 percent of the volume) and the background (comprising 90–95 percent of the volume). This a priori knowledge provides the following two crucial observations. First, it is observed from FIG. 6 that the attenuation coefficient numbers for the three classes are all significantly higher than those for cotton. Therefore, the mean attenuation coefficient value as computed for a contaminated cotton sample would most certainly be higher than that computed for a clean sample of cotton. However, due to the overwhelming majority of cotton in the volume, this value would only be slightly higher than that computed for a sample of pure cotton. Second, it can also be seen from FIG. 6 that there is a significant variation in the attenuation coefficient values among the three classes of trash. In order to see how the dependence of the mean value on the intraclass variations is removed, consider that the contribution of the trash to the computation of the mean value is extremely limited owing to the low trash content. Thus, regardless of the trash present in the volume, the change in the mean value is negligible. This observation is verified by the negligible change in the sample mean value as shown in Table 1.

TABLE 1

Computation of adaptive threshold for volumes of different composition.

| Sample | Sample Composition | Sample mean value | Mean value (cotton) | Std. Dev. (cotton) | Threshold |
|---|---|---|---|---|---|
| 1 | Seed-coat fragments, bark, polypropylene | 0.0096 | 0.0025 | 0.02 | 0.08 |
| 2 | Seed-coat fragments | 0.0105 | 0.0025 | 0.0225 | 0.09 |
| 3 | Polypropylene | 0.0095 | 0.0025 | 0.02 | 0.08 |

Figure 7:
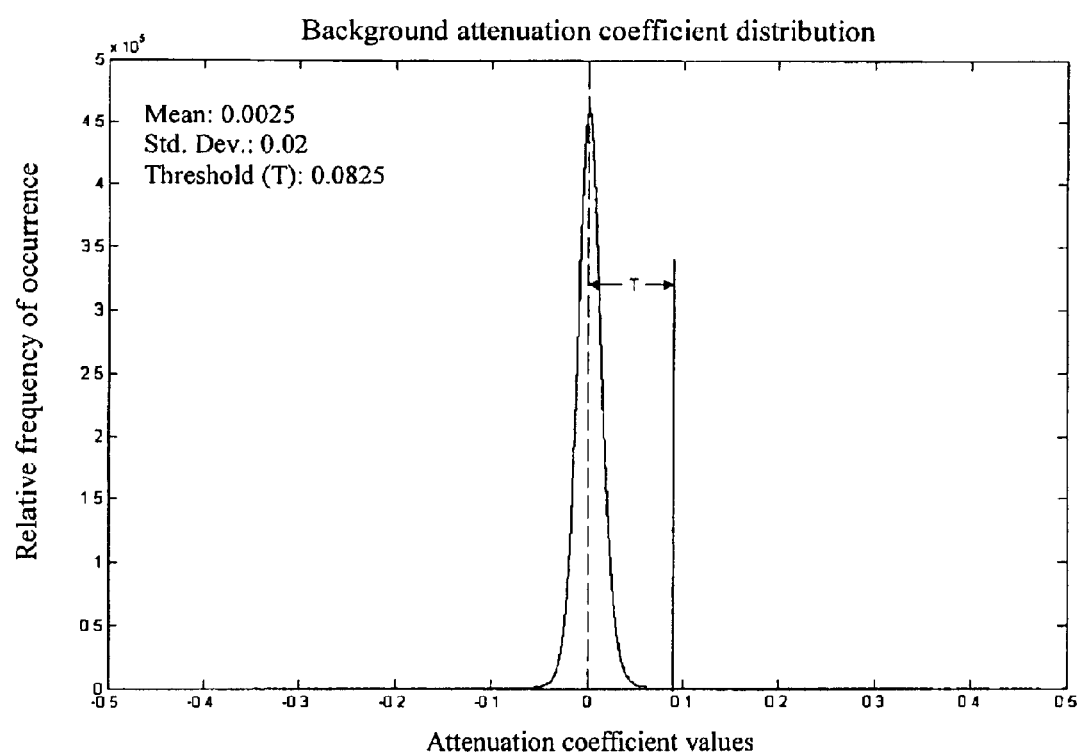
FIG. 7 is a histogram of the saved attenuation coefficient values.
Figure 8:
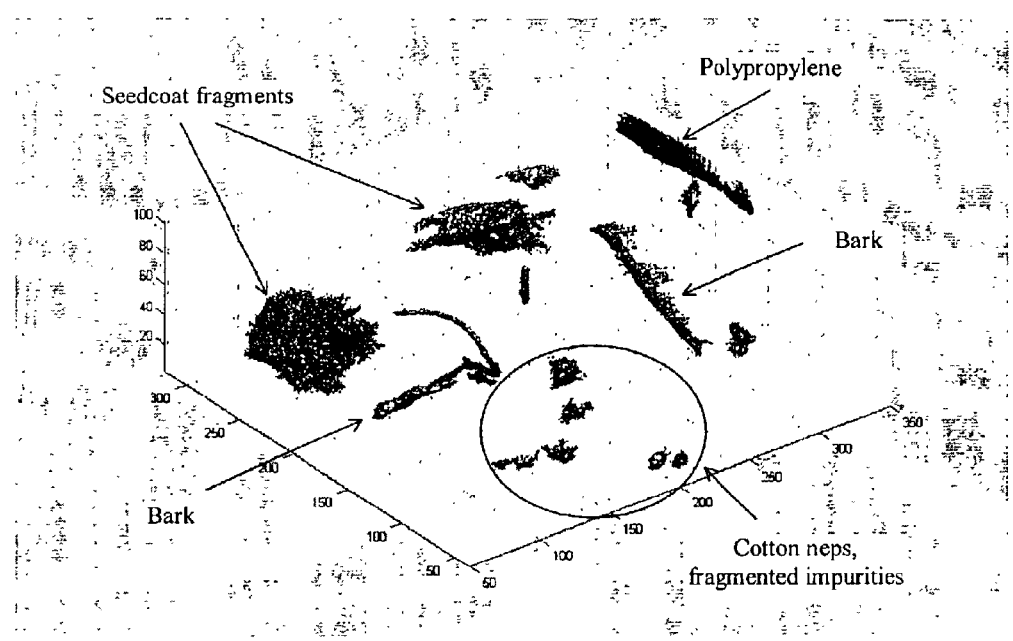
FIG. 8 is a graph showing segmentation by threshold application.

The procedure then used for calculating the threshold is as follows:
1. Compute the mean value for the entire volume.
2. Fragment the entire volume into non-overlapping blocks of size l×m×n. The purpose of fragmenting the volume into blocks is to isolate the blocks which are known to contain only the background. After a number of trials with different values of l, m, and n, it was determined that the size of a block is a variable entity, and may be changed without any noticeable effect on the output of the algorithm.
3. If the mean value of a block is lower than the mean value of the entire volume, save the attenuation coefficient values within that block. This ensures that the values saved represent only the background, since the presence of trash would considerably raise the mean value of the block. It is here that a restriction may be imposed on the size of a data block, since a large block size might cause the presence of trash in a majority of the blocks, resulting in failure of the algorithm.
4. From the histogram for the saved attenuation coefficient values, compute the mean and standard deviation of the distribution. Such a histogram is plotted in FIG. 7. It can be seen that it very nearly resembles a normal distribution, and may be characterized by its mean and standard deviation.
5. Set the threshold at a distance of 4 standard deviations from the mean. For a normal distribution, the area under the curve from a distance of greater than 4 standard deviations from the mean to infinity is negligible. It is thus ensured that the choice of threshold eliminates the presence of the background cotton, and allows for the adaptive segmentation of the trash. The result of the application of such a threshold is shown in FIG. 8.

Effects of Segmentation

As mentioned earlier, a volume scan at low energy levels results in an increase in the perceived attenuation coefficient values and a corresponding increase in contrast. This phenomenon, however, causes the appearance of a number of smaller impurities in the background cotton, as seen in FIG. 8. The majority of these impurities are either cotton neps (usually spherically shaped), or the fragmented remnants of larger impurities that have endured the entire cleaning process. Neps are a source of much concern to the cotton industry due to their resistance to the dying process and the problems caused in yarn formation. The ability to locate and quantify them may prove to be a valuable tool to the cotton industry. Furthermore, their detection enables assessment of the effectiveness of the cleaning methods currently employed.

Figure 9:
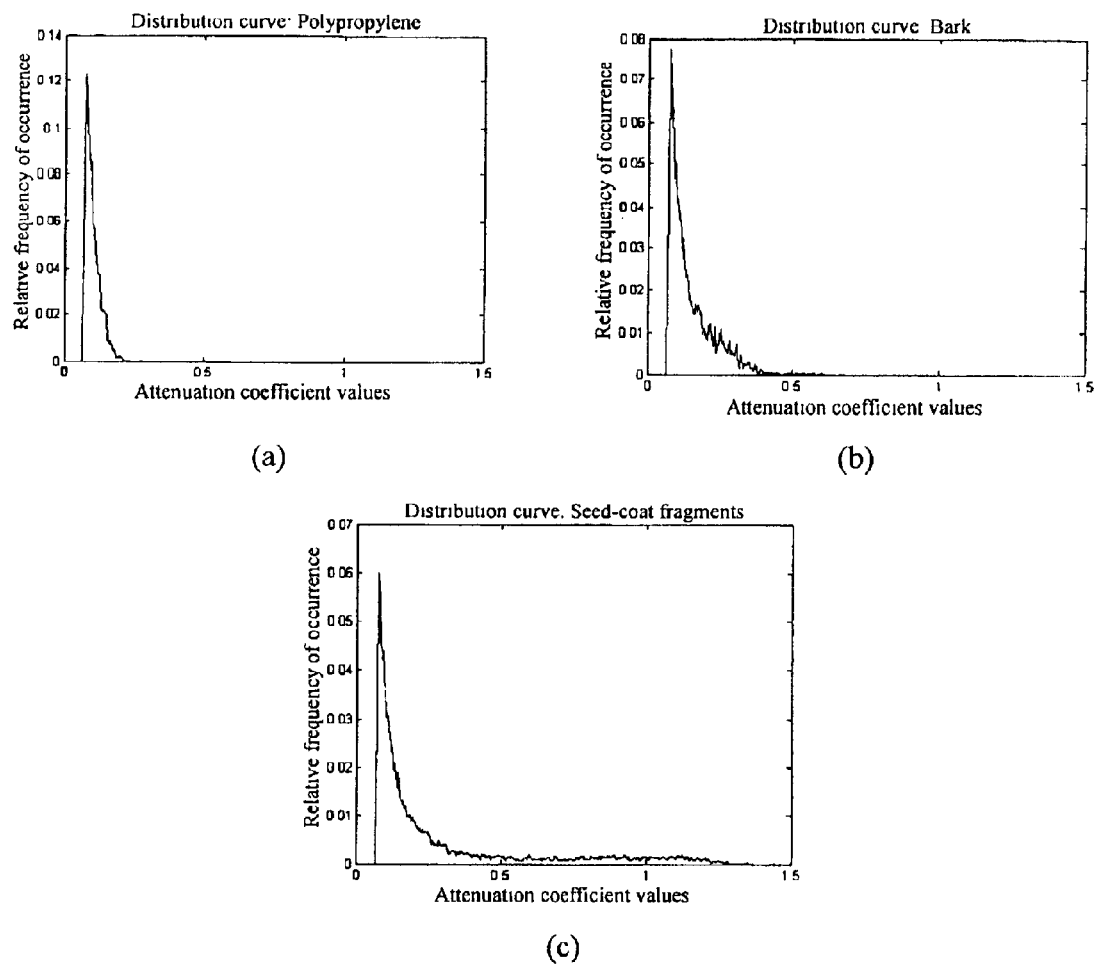
FIG. 9 is a graph of the distribution curves caused by segmentation via thresholding a volume: a) polypropylene; b) bark; and c) seed-coat fragments.
Figure 10:
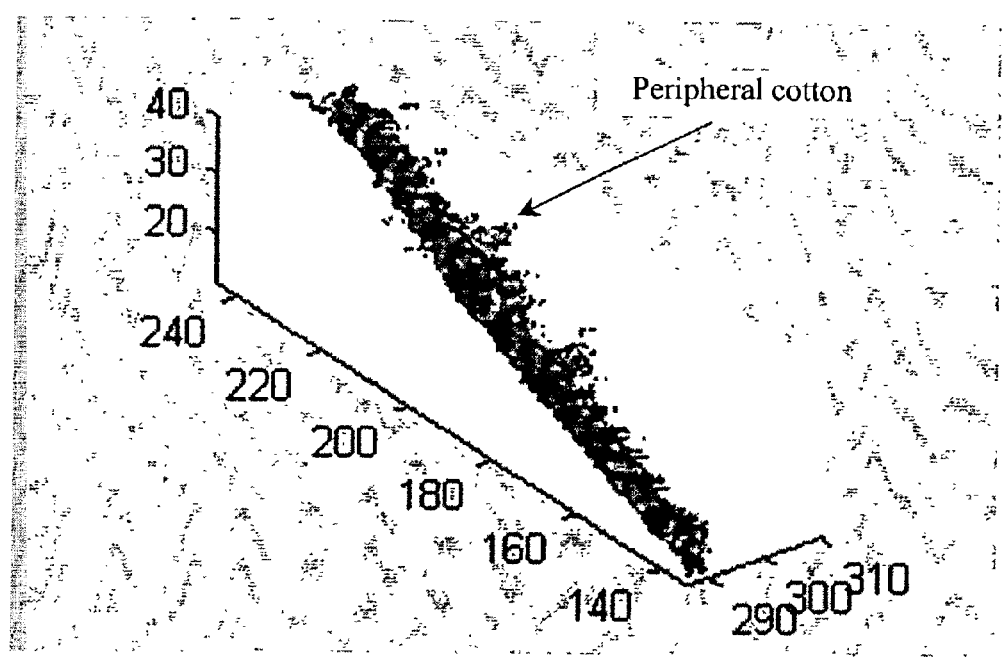
FIG. 10 is a graph showing how the presence of peripheral cotton distorts the volume boundaries of the trash.

A serious problem caused by segmentation via thresholding a volume is a visible distortion of the distribution curves for the classes of trash, as seen in FIG. 9. When a piece of trash is placed in cotton, the pressure created by the cotton pushing against the sides of the trash causes the density of cotton surrounding the trash to increase. This results in the inclusion of some of the background cotton along with the trash when the threshold is applied. This unwanted cotton, henceforth referred to as "peripheral cotton" causes two distinct problems. First, from the curves of FIG. 6, it was determined that the distributions for the three classes could be modeled mathematically. However, due to the distortion introduced in the low end of the attenuation coefficient distribution curves by the presence of peripheral cotton, mathematical modeling of the curves was no longer possible. Second, since the trash is surrounded by peripheral cotton (more or less equally) in all directions, it causes a distortion of the surface features of the trash, as shown in FIG. 10. This disallows the use of surface-analysis features in the classification procedure.

3. Feature Extraction

The preferred x-ray CT scanner, SkyScan-1074, uses a point source and a fixed detector bank for the generation of projections. The projections are reconstructed as slices using the fan-beam convolution backprojection algorithm. The slices are then stacked one on top of each other to obtain a three-dimensional volume. Given this setup, two primary areas exist from which features may be extracted, i.e. the attenuation coefficient (intensity) values, and the spatial (shape) information. The goal then was to be able to extract features that could be used to classify the three types of trash (four, including cotton neps) with a high degree of accuracy. An explanation of the features used for the same is provided below.

Attenuation Coefficient Distribution

Figure 11:
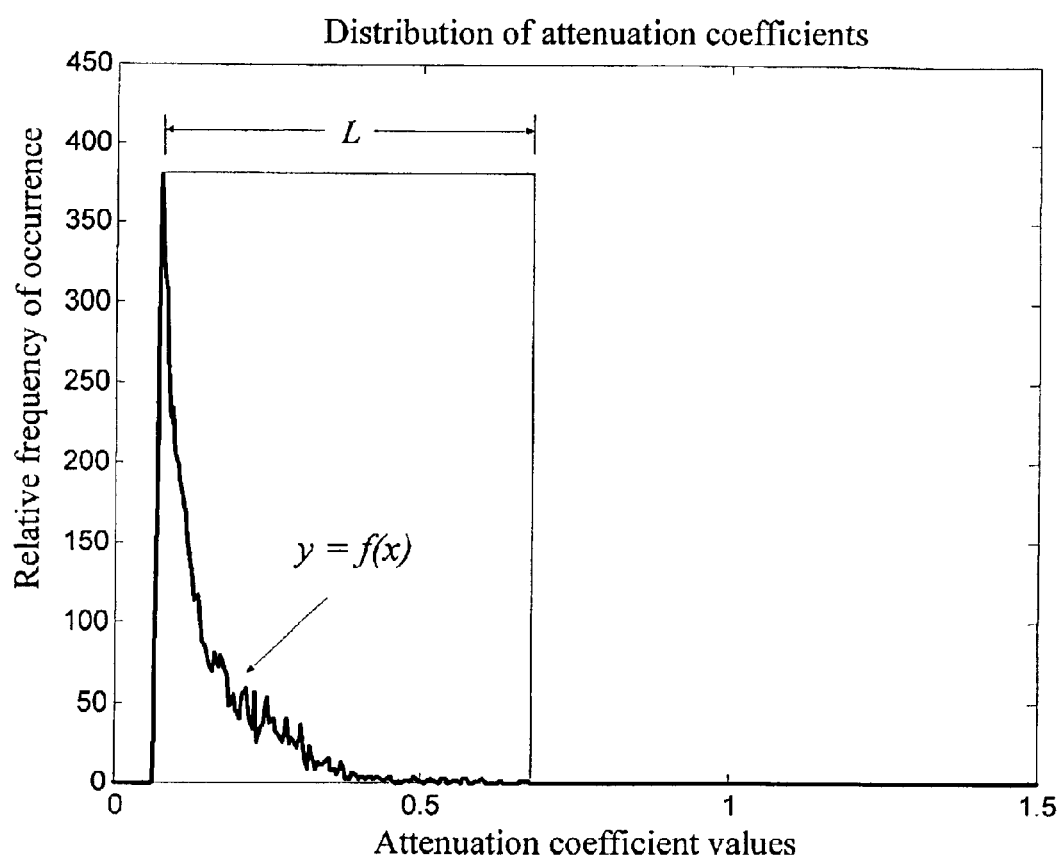
FIG. 11 shows a graph of the attenuation-coefficient based feature extraction.

As explained above, the adaptive thresholding procedure gives rise to a visible distortion in the distribution curves of the attenuation coefficient values, disallowing any form of simple modeling. The only common trend that was observed was the distinct shape and low spread of the polypropylene distribution. It was therefore decided to use attenuation coefficient distributions in their present form for the separation of polypropylene and cotton neps (the other low-density class) from the other classes. This was achieved by noting that of the three classes of trash, polypropylene has a distribution that most nearly resembles a uniform distribution as shown in FIG. 9. Therefore, a feature that describes how much a given distribution curve is similar to a uniform distribution could be used effectively to separate polypropylene. Secondly, the feature chosen should account for the fact that polypropylene and cotton neps have a distinctly low spread in attenuation coefficients. Such a feature is obtained as follows and demonstrated in FIG. 11. Once the attenuation coefficient distribution curve of a trash sample is obtained, it is truncated so that only the non-zero elements of the curve remain. Therefore, if f(x) represents the distribution curve for the trash, then $$y = f(x), f(x) \neq 0 \quad (4)$$

where $y = \{y_1, y_2, \ldots, y_L\}$ is a vector of variable length L. Next, the vector y is normalized so that all its elements lie in the range [0, 1], i.e., $$y_{norm} = \frac{y}{\max(y)} \quad (5)$$

The vector $y_{norm}$ represents a normalized, truncated version of the attenuation coefficient distribution curve calculated for the given trash sample. The feature then extracted for the purpose of classification is the mean value of the vector $y_{norm}$, i.e., $$\overline{y}_{norm} = \sum_{i=1}^{L} [y_{norm}(i) \cdot P_{y_{norm}}(i)] \quad \text{where,} \quad (6)$$

$$P_{y_{norm}} = \frac{y_{norm}}{\sum_{j=1}^{L} y_{norm}(j)} \quad (7)$$

represents the probability density function of the vector $y_{norm}$.

Two points of interest are made here. First, it is noted that since the curve is normalized to range from zero to unity, the value of the mean will always be in the range [0, 1]. Second, the compact nature of the polypropylene distribution as seen in FIG. 9 ensures that the vector $P_{y_{norm}}$ would produce consistently higher numbers than in the case of bark and seed-coat fragment distributions.

Figure 12:
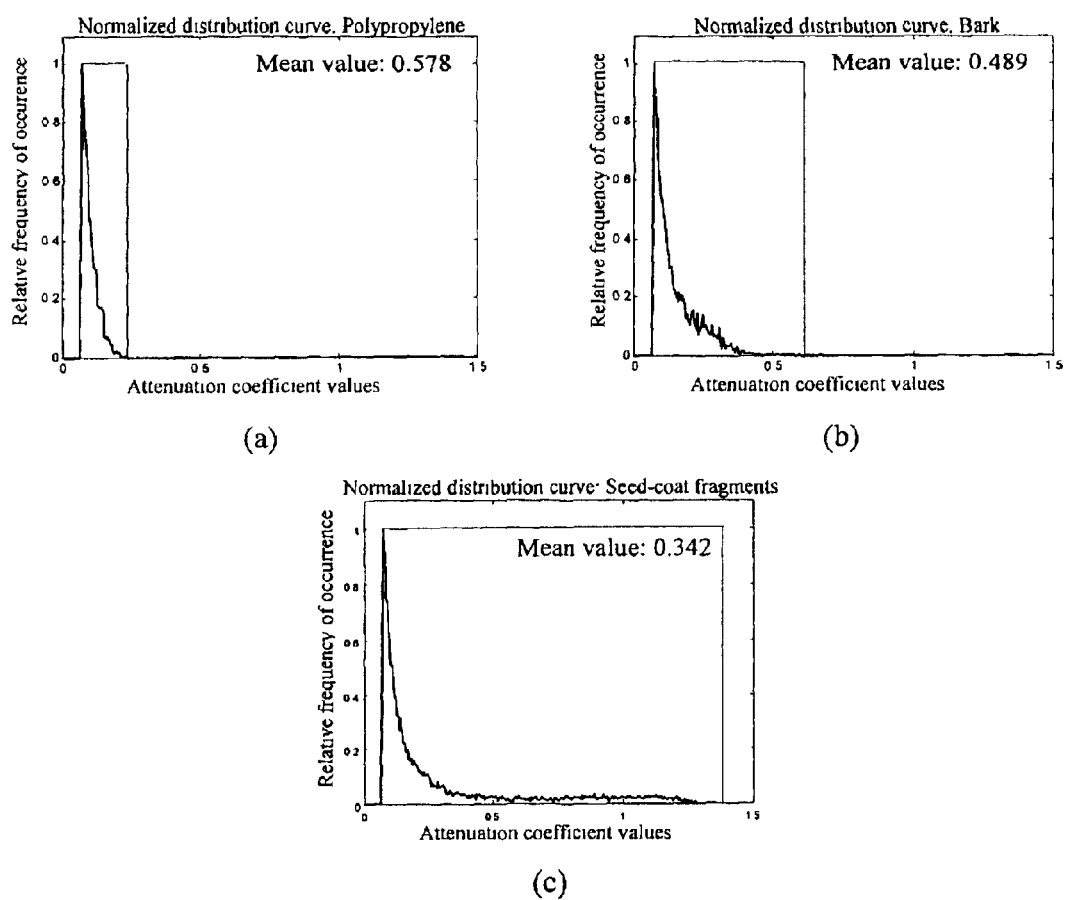
FIG. 12 show normalized distribution curves for the three classes of trash: a) polypropylene; b) bark; and c) seed-coated fragments.

It is easy to see that if the curve in question is identical to a uniform distribution, then the mean will be unity. The operation of this feature is demonstrated by a few examples, as shown in FIG. 12. The three graphs shown in FIG. 12 represent distribution curves (normalized so that their peaks lie at unity) belonging to the three classes of trash, and are roughly representative of their classes. FIG. 12(a) shows a representation of the distribution curve for polypropylene. FIG. 12(b) shows a representation of the distribution curve for bark. FIG. 12(c) shows a representation of the distribution curve for seed-coat fragments. It is evident from these graphs that the mean value increases for classes of trash that show a low variation on attenuation coefficient numbers, and decreases as the variation within a trash type increases. It will be shown below that this feature may be used very effectively in separating the low average attenuation trash types, such as polypropylene and cotton neps, from those with higher attenuation coefficients, such as bark and seed-coat fragments. Since this particular feature is dependent solely on the distribution of the attenuation coefficient values, the expected values for cotton neps are very similar to those of polypropylene.

Elongation

As explained earlier, the peripheral cotton causes a general blurring of the surface features, rendering surface texture analysis ineffective. However, this peripheral cotton surrounds the trash sample uniformly in all directions, and therefore does not greatly affect the general shape of the trash. Therefore, for the purpose of feature generation, it was decided to examine the characteristic shapes of trash samples from the three classes.

The choice of the three classes, polypropylene, bark, seed-coat fragments, is justified by their resistance to the cleaning process. Seed-coat fragments are created when cottonseeds are accidentally crushed in the ginning process. Referring to FIG. 8, it is seen that the fragments are generally small and compact, and are covered on the outer surface by cotton fibers that are short and dense. The entanglement of these fibers with the longer fibers of the peripheral cotton is what gives the seed-coat fragments their resilience. Furthermore, the short fibers, which are segmented as a part of the seed-coat fragments, cause the fragments to have an almost rounded, fuzzy shape. Also evident from FIG. 8, this rounded shape is also seen consistently in cotton neps.

In sharp contrast to this, the bark and polypropylene are fibrous in nature. The long and thin shape of these classes causes them to assume the shape characteristics of cotton fibers, and thus survive the cleaning process. The inherent elongation of the samples of these classes separates them from seed-coat fragments and cotton neps. A measure of the elongation is then calculated using the Hotelling Transform, also known as Principal Component Analysis, and is based on the statistical properties of vector representations.

The three-dimensional coordinates of the voxels constituting the trash sample are treated as random variables, and are represented by the three-dimensional vector $$x = [x \ y \ z] \tag{8}$$

where x, y, and z represent the coordinates in the spatial domain. The mean vector of this vector population is defined as $$m_x = E\{x\} \tag{9}$$

where $E\{\ \}$ is the expected value of the argument. The covariance matrix is calculated as $$C_x = E\{(x-m_x)(x-m_x)^T\} \tag{10}$$

where T indicates vector transposition. Because x is three-dimensional, $C_x$ is a matrix of order 3×3. Element $c_{ii}$ of $C_x$ is the variance of $x_i$ and element $c_{ij}$ of $C_x$ is the covariance between elements $x_i$ and $x_j$ of these vectors. The matrix $C_x$ is real and symmetric.

Figure 13:
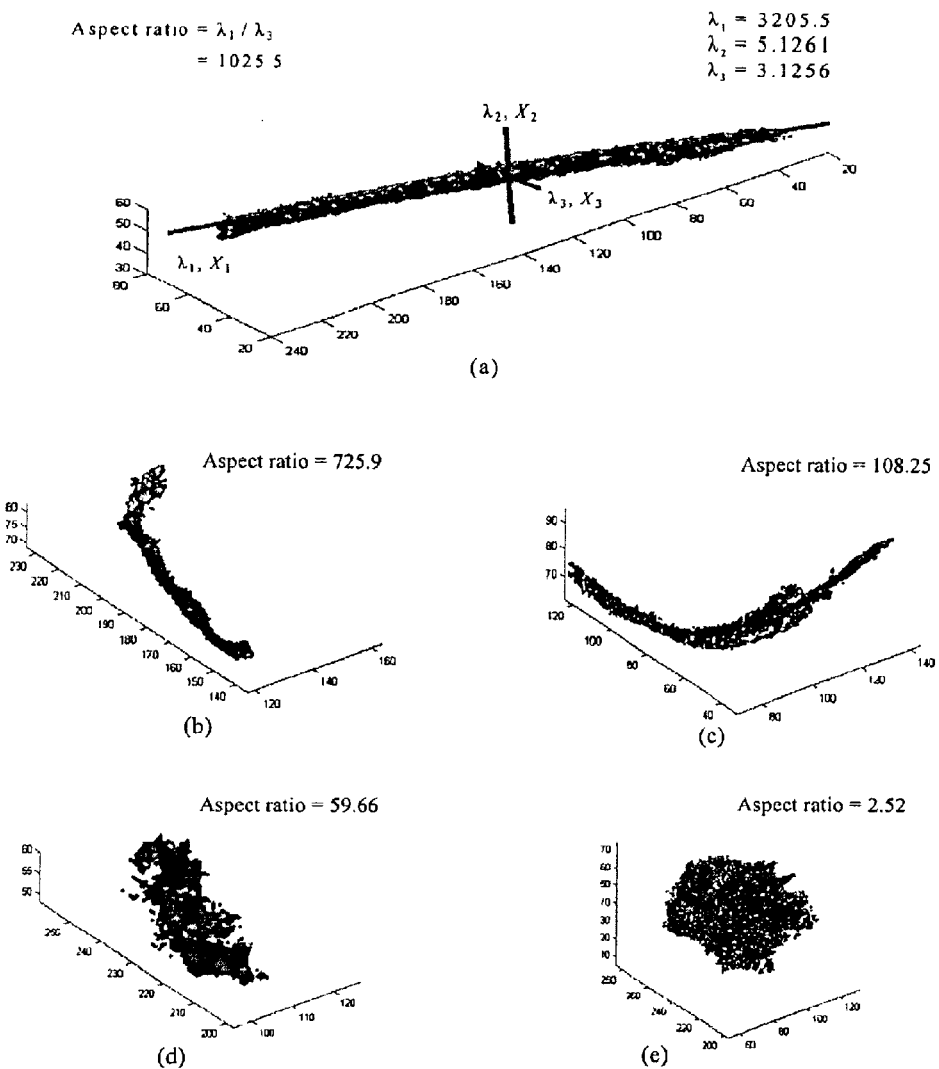
FIG. 13 shows the corresponding eigenvalues of the covariance matrix.

The eigenvectors and eigenvalues of the matrix are obtained from the solution of the equation $$C_x X = \lambda X \tag{11}$$

where $X_i$ {i=1, 2, 3} represents the eigenvectors and $\lambda_i$ {i=1, 2, 3} represents the eigen the matrix $C_x$. The eigenvectors of the covariance matrix represent the directions of the three axes along which the voxels have a maximum spread or greatest variance, as seen in FIG. 13(a). The corresponding eigenvalues give us the relative spread of the object along the three axes in the spatial domain.

The ratio of the maximum eigenvalue to the minimum eigenvalue can be thought of as a measure of the 'length' of the object to its 'width'. This ratio is called the Aspect ratio, and is defined as $$\text{Aspect ratio} = \frac{\lambda_{max}}{\lambda_{min}} \tag{12}$$

The operation of this feature is illustrated by examples shown in FIGS. 13(b)–(e). It can be seen that as the elongation of the object decreases, there is a corresponding decrease in the aspect ratio. The aspect ratio, as will be shown later, can be used very effectively with the first feature, i.e., the distribution curve ratio, to effectively classify the trash into four groups. The classifier used to analyze and classify these features is described below.

4. Feature Analysis and Classification

The final stage in the design of an image-based classification system is feature analysis and classification. It is in this stage that the features measured for a given object are analyzed using one of many available classification algorithms. The output of the classification algorithm is a label that qualifies the object as belonging to one of a number of classes. The classification algorithms may be based either on certain a priori information about the classes (rule-based classification), or it may be based purely on the distribution of the features in the feature space.

Given the nature of the problem, and the relatively large amount of information already known about the trash types, it is easy to see that an optimal classification scheme would involve the use of a rule-based classifier. For instance, it is known that the polypropylene would have a high value of distribution curve ratio, and a high aspect ratio. Such rules may be used in a rule-based classification scheme, and it will be shown below that such a classification can be used to effectively classify trash. However, a major flaw in such a scheme is that the rules are based entirely upon rigid thresholds and, unless the features offer excellent separation, it may be prone to failure. The rules and the thresholds used are determined by the extensive testing of many objects, and are therefore very specific to the problem. Furthermore, such a scheme is inflexible to the addition of other classes.

In view of these shortcomings, what is preferred is a classification algorithm that is rule-based, and yet is generalized enough to be extended to include more classes without rigorous testing and intricate thresholding procedures. Such a solution is offered by the use of a preferred fuzzy logic based classifier. Fuzzy logic provides a good blend of rule-based classification with the flexibility to include many classes of data, and is relatively simple, both in concept, and in implementation.

A great advantage of using fuzzy logic over hard-threshold-based classification schemes is that fuzzy logic intuitively lends itself to the problem at hand. Given the fact that a majority of the trash classes dealt with, such as bark, seed-coat fragments, and cotton neps, are organic in nature, it is reasonable to expect a large variation in shapes and attenuation coefficients of objects belonging to each class. This is reflected in the observed overlap between the various classes. Thus, in the absence of a crisp distinction between the four classes (including cotton neps), it makes logical sense to use a classification procedure that provides us with information about the partial membership of a given object to a class, i.e., to what class the particular object most likely belongs.

It will be shown below that a fuzzy logic-based classifier may be used very effectively to classify the four classes of trash found in cotton. The output of the fuzzy classifier provides information about how much an object belongs to each of the four classes. This information is then used to make an accurate judgment of the final classification of the object. It is instructive to reiterate at this point that the choice of a fuzzy classifier is based on the fact that new classes of trash may be added easily, and the classification strategy may be extended to include more classes without much change in procedure.

EXAMPLE

The approach used for the detection of cotton contaminants in a cotton sample will be to describe the process of acquisition, segmentation, feature extraction, and finally classification, as used to evaluate fifty volumes that were contaminated by 162 pieces of trash of known classification.

1. Sample Preparation

Each of the fifty test samples was prepared using cleaned D6 variety cotton for the background. This variety of cotton possesses a bare seed, marked by the absence of short fibers on the seed-coat exterior, and therefore the cleaned cotton is relatively free of fragmented impurities. The samples of trash introduced in the pure cotton were obtained from a bale of ginned cotton, and were selected to span the entire gamut of shapes, sizes, and thickness. The trash introduced, however, belonged only to the following three classes: seed-coat fragments, bark, and polypropylene. Samples belonging to the fourth class, cotton neps, are inherent to ginned cotton and to a lesser extent to cleaned cotton. Consequently, they could not be introduced into cleaned cotton in a controlled fashion. It is known, however, that cotton neps possess polypropylene-like attenuation coefficient numbers and small, spherical shapes. This knowledge about cotton neps allows for their inclusion into the preferred fuzzy classification procedure.

2. Volume Acquisition

Figure 14:
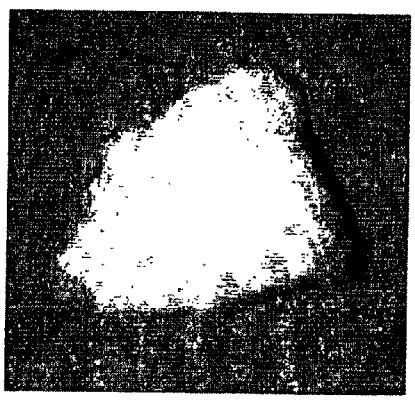
FIG. 14 show images of trash containing cotton samples: a) a surface scan of the cotton sample and b) a radiographic image of the cotton sample.
Figure 14:

The volume of cotton shown in FIG. 14 was contaminated by four pieces of trash, belonging to the three trash classes. FIG. 14(a) shows a surface scan of the cotton sample with no indication of any buried trash. A radiographic image of the sample is shown in FIG. 14(b). The region of interest containing the trash, as indicated by the rectangle in FIG. 14(b), was scanned at a tube energy setting of 20 kV and 1000 $\mu$A, using 200 projections.

The projections being acquired, the sample was reconstructed using the software provided with the scanner hardware using a fan-beam filtered backprojection algorithm.

For the given region of interest, the size of the volume formed by stacking the reconstructed slices was found to be roughly of the order of 700×700×100 voxels. Furthermore, the attenuation coefficient numbers for each voxel, as output by the reconstruction software, were represented using four-byte floating-point format. This placed a tremendous computational burden on the processor, and severely restricted overall efficiency. Therefore, it was determined that the reconstructed slices be subsampled prior to any processing. It was experimentally determined that for the three classes in question, subsampling the slice data could be performed without significant loss of information.

3. Volume Analysis

The procedure adopted for processing the sample is outlined in the flowchart of FIG. 1. The subsampled, integer slice data was then presented to a computer program where all further processing and analysis are carried out. The slices are processed using the preferred interactive GUI-based application shown in FIG. 15. The various functions available for the analysis of a given volume and the steps taken to classify the trash are labeled numerically in their order of precedence.

Figure 15:
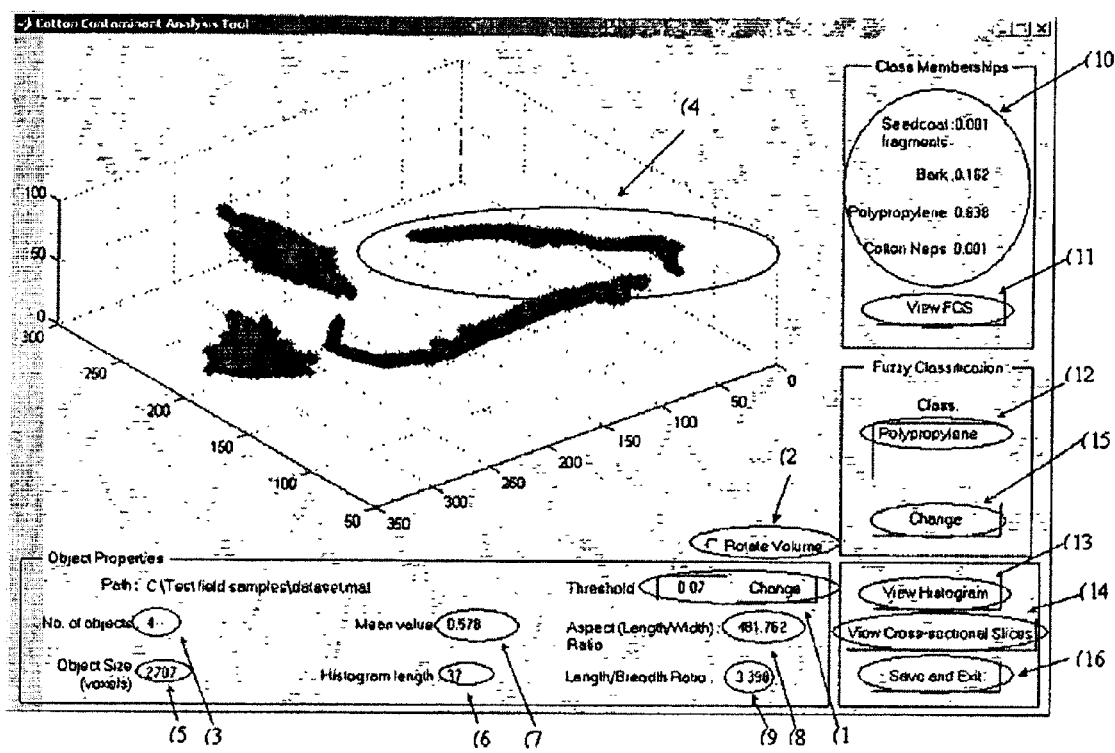
FIG. 15 shows an interactive GUI-based application for the present invention.

The application starts by loading the slice data, and stores the unsegmented volume data in a three-dimensional matrix. Next, the automated, adaptive thresholding algorithm is applied to the volume, and an optimal value for the threshold 1 is determined. The data block size of 16×16×16 was experimentally determined to be adequate for the adaptive thresholding procedure. The result of thresholding the volume is plotted in the viewing area as shown in FIG. 15. If this result is found to be unsatisfactory, the threshold may be changed using the option provided. The resulting volume is then plotted in the viewing area. Prior to plotting this volume, however, a size filter is applied to the volume to remove any particulate impurities. The purpose of this filter is purely to speed up the processing of the volume, and it may be avoided. The value of this size filter was based on the fact that the size of all the objects of trash belonging to the three classes were known to be greater than 200 voxels. It should be noted at this point that this implementation deals strictly with the evaluation of ginned cotton. In the event that this implementation is to be applied to the detection of fragmented impurities in processed cotton, the size filtering should be either modified or entirely avoided. The plotted volume may be rotated 2 to afford the user the best possible view. The objects 3 present in the field of view may then be interactively selected 4 using the cursor. Upon doing so, the necessary measurements are made from the object. These include the object size 5 in voxels, and the attenuation coefficient distribution curve. From the distribution curve, the histogram length 6, and the distribution curve ratio 7 are computed. Next, from the voxel coordinates, the aspect (length/width) ratio 8, and the length/breadth ratio 9 are computed.

4. Fuzzy Classification

Figure 16:
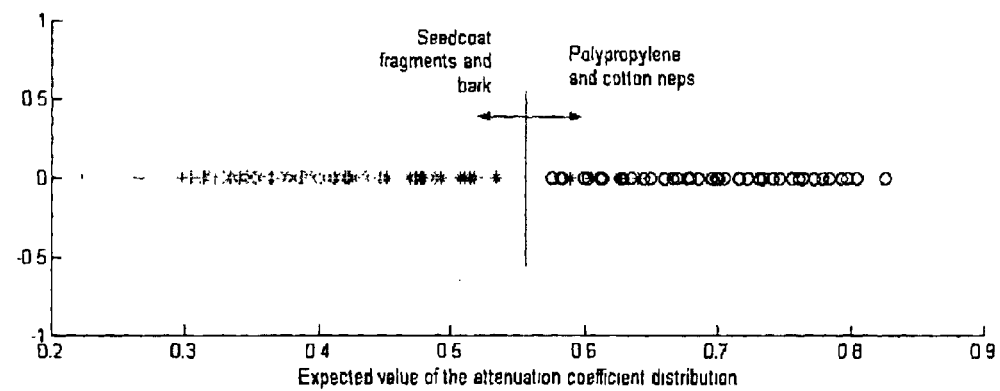
FIG. 16 shows measurements of features for 162 samples of known classification: a) shows the mean value of the truncated normalized distribution and b) shows aspect ratio measurements.
Figure 16:
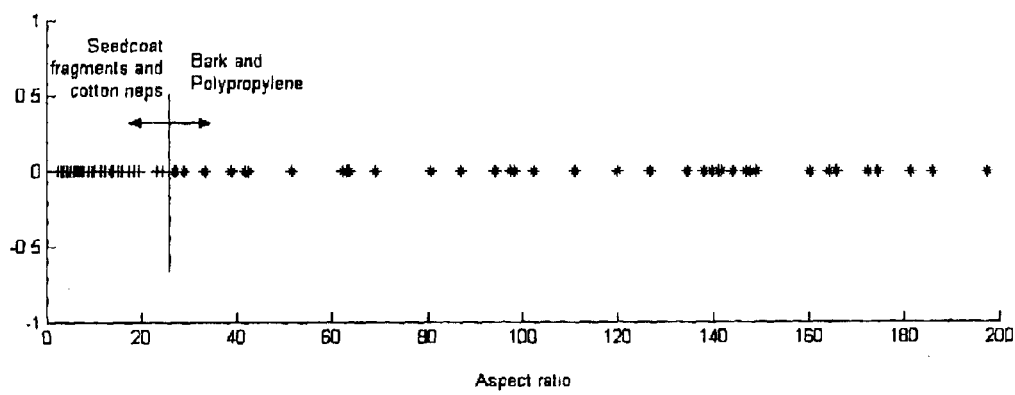

The distribution curve ratio and the aspect ratio are then used in a two-feature, fuzzy logic based classifier. The fuzzy classifier was implemented using a computer program. The distributions of the two features as measured from the fifty volumes are shown in FIG. 16. FIG. 16(a) shows the mean value of the truncated normalized distribution and displays two almost compact clusters, with excellent separation. The aspect ratio measurements show that compactly shaped rounded trash types (seed-coat fragments, and cotton neps) have a very small aspect ratio, as opposed to bark and polypropylene, which display a much larger spread, see FIG. 14(b). The plot has been truncated to show values of aspect ratio between the range 0–200.

The if-then rules used in the classifier were generated from the plots as are stated as follows:

1. "If mean value is low and aspect ratio is low, then seed-coat fragments is high, bark is low, cotton neps is low, polypropylene is low."

2. "If mean value is low and aspect ratio is high, then seed-coat fragments is low, bark is high, cotton neps is low, polypropylene is low."

3. "If mean value is high and aspect ratio is low, then seed-coat fragments is low, bark is low, cotton neps is high, polypropylene is low."

4. "If mean value is high and aspect ratio is high, then seed-coat fragments is low, bark is low, cotton neps is low, polypropylene is high."

Figure 17:
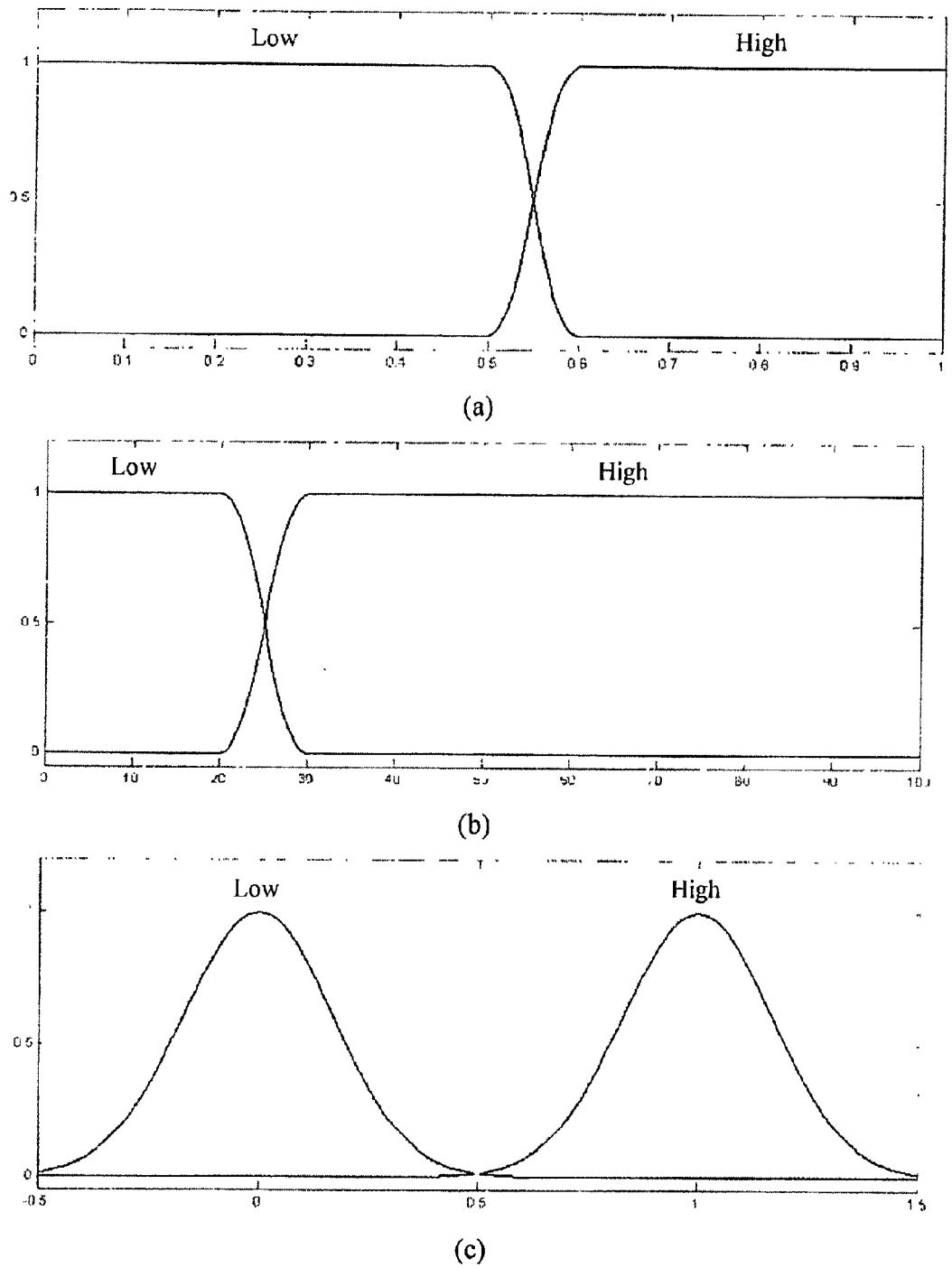
FIG. 17 shows a new membership class added to the fuzzy classifiers.

The membership functions used to define the linguistic variables (fuzzy subsets) high and low for the two features and the four output classes are shown in FIG. 17. FIG. 17(a) shows the mean value of the normalized truncated histogram. FIG. 17(b) shows the aspect ratio. FIG. 17(c) shows all of the four classes: seed-coat fragments, bark, polypropylene, and cotton neps. When presented with the two features measured for an object 10, the classifier produces four outputs. These numbers lie in the range [0, 1] and indicate the degree to which the object belongs to each of the four classes. An option 11 has been provided so that changes in the fuzzy classifier (the if-then rules, or the membership functions) may be effected by the user.

If a given object is classified as belonging to a particular class to a degree greater than 0.7, then the object is labeled 12 as belonging to that particular class. However, should the outputs of the classifier be ambiguous, the object is indicated as belonging to either one of two, or four classes. In this case, the user is provided the option of changing the classification 13. In order to make this change, the user may avail of any of the three-dimensional representation (in the main plot), the attenuation coefficient distribution curve 14, or planar profiles of the object 15. These profiles are taken along planes that pass though the object centroid, and are perpendicular to the object's principal component axes, as shown in FIG. 13(a). Once all the requisite measurements have been made, they may be saved 16 in the computer workspace file and may be accessed at a later time.

5. Results

The results obtained by performing the above procedure on 162 trash samples belonging to the three classes are summarized using a confusion matrix in Table 2. The rows of Table 2 indicate the inputs of known classification, whereas the columns represent the classes as assigned by the classifier. The sum of any row indicates the total number of samples of a particular class that were input to the system. For instance, the first row shows that a total of 46 (=44+1+1) samples of bark were presented to the classifier. Of these samples, 44 were correctly classified as bark, 1 sample was classified as seed-coat fragment, and 1 was classified as being ambiguous (bark/seed-coat fragment).

TABLE 2

Summary of results after classification of 162 trash samples.

|  | Bark | Poly. | Seed-coat frag | Cotton neps | Bark/ Seed-coat frag. | Bark/ Poly. | Cotton neps/ Poly. | All |
|---|---|---|---|---|---|---|---|---|
| Bark | 44 | 0 | 1 | 0 | 1 | 0 | 0 | 0 |
| Poly. | 0 | 49 | 0 | 0 | 0 | 0 | 0 | 0 |
| Seed-coat frag. | 1 | 0 | 64 | 0 | 2 | 0 | 0 | 0 |

Ideally, a confusion matrix is a square matrix, containing an equal number of rows and columns. However, it is seen in this case that the number of output classes is greater than the number of input classes. This produces a matrix with more columns than rows. It can also be seen that no input samples belonging to the class 'cotton neps' were presented to the classifier. This relates to the fact that the occurrence of cotton neps in cleaned cotton is erratic, and cannot be controlled. Hence, although a given sample may possess the characteristics of cotton neps (low-density, spherical shape), this could not be verified easily.

It can be seen from Table 2 that of 162 input samples, 157 samples were correctly classified. This translates to a correct classification percentage of 96.91%.

6. Fuzzy Classifiers and their Advantages

As can be seen from FIG. 16, hard thresholds may be used to classify the trash very accurately into the four classes. However, a hard-threshold-based classification scheme suffers from the disadvantage of possible incompatibility to the addition of more classes. This disadvantage may be overcome easily by the use of a fuzzy classification scheme, as is illustrated by the following hypothetical example.

Figure 18:
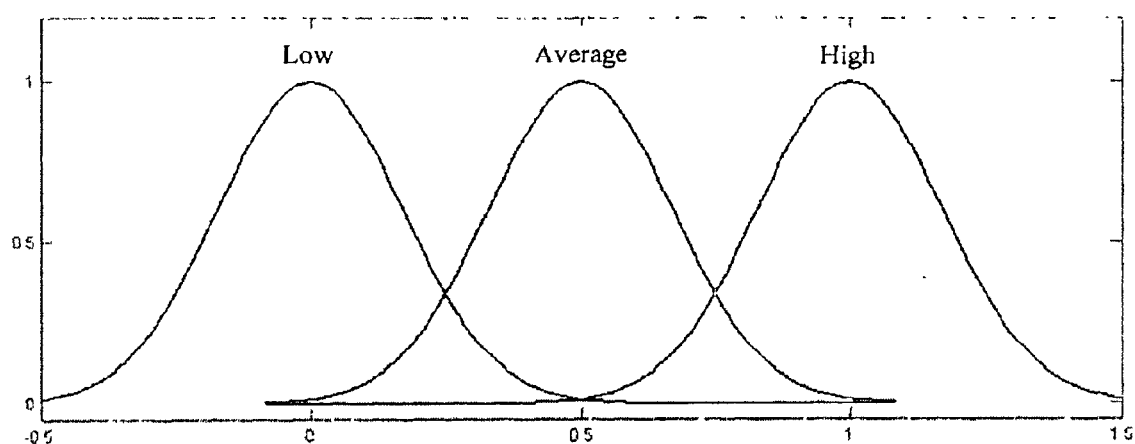

Let us suppose that it is desired to introduce a fifth class of trash, X. It is known that the class X possesses mean values intermediate to those of polypropylene (high), and seed-coat fragments and bark (low). It is also known that class X possesses aspect ratios intermediate to those of polypropylene and bark (high), and seed-coat fragments (low). With reference to FIG. 16, it can be easily seen that a threshold-based scheme would probably fail in such a situation for the lack of a suitable threshold. However, in the fuzzy classifier, a new membership function may be introduced for each output variable as seen in FIG. 18 and change the corresponding if-then rules. An example of a changed if-then rule might be: "If mean value is average, and aspect ratio is average, then seed-coat fragments is low, bark is low, cotton neps is low, polypropylene is low, X is high."

It is obvious that the introduction of a new class would reduce the accuracy of the classification procedure regardless of which classification strategy is used, but the advantage of using a fuzzy classifier lies in the fact that the general procedure used will remain the same, and may be extended to the addition of classes. If a new feature were added, then only a simple change in the if-then rules and the output membership functions would be needed for the correct operation of the classifier.

Although the present invention has been disclosed in terms of a preferred embodiment, it will be understood that numerous additional modifications and variations could be made thereto without departing from the scope of the invention as defined by the following claims:

What is claimed is:

1. A method for classifying a cotton contaminant in a cotton sample, comprising
   a) acquiring a tomographic image of said cotton sample using an x-ray scanner;
   b) segmenting said tomographic image to isolate said cotton contaminant;
   c) extracting a feature from said cotton contaminant;
   d) analyzing said feature using a classification algorithm; and
   e) classifying said cotton contaminant based on said classification algorithm.

2. The method of claim 1, wherein said cotton contaminant is selected from the group consisting of seed-coat fragments, bark, cotton neps and polypropylene-based plastics.

3. The method of claim 1, wherein said classification algorithm is a rule-based algorithm.

4. The method of claim 3, wherein said rule-based algorithm is fuzzy logic.

5. The method of claim 1, wherein said tomographic image is a microtomographic image.

6. The method of claim 1, wherein said x-ray scanner operates at a voltage of 5–40 kV.

7. The method of claim 6, wherein said x-ray scanner operates at a voltage of 20 kV.

8. The method of claim 1, wherein said feature is selected from the group consisting of an attenuation coefficient and an aspect ratio.

9. The method of claim 1, wherein said step of segmenting includes isolating said cotton contaminant based on a threshold value.

10. The method of claim 9, wherein said threshold value is an attenuation coefficient.

* * * * *